US012622624B2

(12) United States Patent
Guimera Brunet et al.

(10) Patent No.: US 12,622,624 B2
(45) Date of Patent: May 12, 2026

(54) ACQUISITION DEVICE TO LIMIT LEAKAGE CURRENT IN ELECTROPHYSIOLOGICAL SIGNAL RECORDING DEVICES

(71) Applicants: CONSEJO SUPERIOR DE INVESTIGACIONES CIENTÍFICAS, Madrid (ES); CONSORCIO CENTRO DE INVESTIGACION BIOMEDICA EN RED, M.P., Madrid (ES); ICREA, Barcelona (ES); INSTITUT CATALÀ DE NANOCIÈNCIA I NANOTECNOLOGIA (ICN2), Barcelona (ES)

(72) Inventors: Antón Guimera Brunet, Barcelona (ES); Lucía Re Blanco, Barcelona (ES); Eduard Masvidal Codina, Barcelona (ES); Rosa Villa Sanz, Barcelona (ES); Xavier Illa Vila, Madrid (ES); José Antonio Garrido Ariza, Barcelona (ES); Nathan Schaefer, Barcelona (ES); Ramón García Cortadella, Barcelona (ES)

(73) Assignees: CONSEJO SUPERIOR DE INVESTIGACIONES CIENTÍFICAS, Madrid (ES); CONSORCIO CENTRO DE INVESTIGACION BIOMEDICA EN RED, M.P, Madrid (ES); ICREA, Barcelona (ES); INSTITUT CATALÀ DE. NANOCIÈNCIA I NANOTECNOLOGIA (ICN2), Barcelona (ES)

( * ) Notice: Subject to any disclaimer, the term of this patent is extended or adjusted under 35 U.S.C. 154(b) by 469 days.

(21) Appl. No.: 18/023,228

(22) PCT Filed: Sep. 17, 2021

(86) PCT No.: PCT/EP2021/075616
§ 371 (c)(1),
(2) Date: Feb. 24, 2023

(87) PCT Pub. No.: WO2022/058496
PCT Pub. Date: Mar. 24, 2022

(65) Prior Publication Data
US 2024/0008789 A1     Jan. 11, 2024

(30) Foreign Application Priority Data
Sep. 17, 2020     (EP) ..................................... 20382819

(51) Int. Cl.
| A61B 5/31 | (2021.01) |
| A61B 5/30 | (2021.01) |
| H03D 1/18 | (2006.01) |

(52) U.S. Cl.
CPC .................. *A61B 5/31* (2021.01); *A61B 5/30* (2021.01); *A61B 2562/046* (2013.01); *H03D 1/18* (2013.01)

(58) Field of Classification Search
CPC ....... A61B 5/31; A61B 5/30; A61B 2562/046; A61B 5/388; A61B 5/301; H03D 1/18
See application file for complete search history.

(56) References Cited

U.S. PATENT DOCUMENTS

| 4,834,103 | A | * | 5/1989 | Heath | .................. | G09B 23/286 |
| | | | | | | 607/152 |
| 2014/0107981 | A1 | * | 4/2014 | Brown | ................... | G01N 37/00 |
| | | | | | | 702/189 |

FOREIGN PATENT DOCUMENTS

| WO | 2020025786 A1 | 2/2020 |
| WO | 2020094898 A1 | 5/2020 |

* cited by examiner

*Primary Examiner* — Tse W Chen
(74) *Attorney, Agent, or Firm* — Hayes Soloway PC

(57) ABSTRACT

The device limits the leakage current in an electronic system for recording electrophysiological signals, where the transducer element is an active device, the device comprising an active transducer (1), intended to contact a human tissue, connected to a transimpedance amplifier (2), and a first resistor (6) connected parallel to the transimpedance amplifier (2), an alternate voltage source (7) and a direct voltage source (8), both connected to the active transducer (1), a first capacitor (3) connected between the alternate voltage source (7) and the active transducer (1), a second resistor (4) connected between the direct voltage source (8) and the (Continued)

active transducer (1), parallel with the first capacitor (3) and the alternate voltage source (7), and a second capacitor (5), connected between the active transducer (1) and the transimpedance amplifier (2).

7 Claims, 10 Drawing Sheets

(STATE OF THE ART)

(STATE OF THE ART)

(STATE OF THE ART)

ACQUISITION DEVICE TO LIMIT LEAKAGE CURRENT IN ELECTROPHYSIOLOGICAL SIGNAL RECORDING DEVICES

CROSS-REFERENCE TO RELATED APPLICATIONS AND PRIORITY

This patent application claims priority from PCT Application No. PCT/EP2021/075616 filed Sep. 17, 2021, which claims priority from European Patent Application No. 20382819.9 filed Sep. 17, 2020. Each of these patent applications are herein incorporated by reference in their entirety.

OBJECT OF THE INVENTION

The invention relates to an acquisition device that limits the leakage current in an electronic system for recording electrophysiological signals where the transducer element is an active device.

BACKGROUND OF THE INVENTION

The limitation of the leakage currents through a patient in electrophysiology signal recording devices is needed to meet with the regulatory laws applied to medical devices (IEC60601), and therefore for the use of the active transducers in clinical applications.

Most of the systems used for recording neural signals are based on electrodes as transducer element. In these systems, neural signal acquisition is based on the amplification of the electrode's voltage, so the acquisition electronic system basically consists on a voltage amplifier with a high input impedance. FIG. 1 shows a schematic of an acquisition system based on electrodes, where measured voltage is controlled by the effective electrode impedance ($Z_{electrode}$) and the effective input impedance ($Z_{in}$).

Unlike these systems, acquisition systems based on active elements need to perform two functions: 1) to polarize the transducer device at an optimal working point, and 2) to amplify the signal proportional to the neural activity recorded by the transducer. FIG. 2 shows a schematic of an acquisition system based on active transducer (gSGFET) represented on the left. $V_{drain}$ and $V_{source}$ voltage sources fix the bias point, and the transimpedance amplifier, represented on the centre of the figure, amplifies the transistor current ($I_{ds}$) which contains the neural signal, which is them processed.

The use of active transducers, specifically ones based on graphene transistors (gSGFETs), have shown several advantages with respect to current technologies based on metal electrodes such as their ability to record very low frequency signals (<0.1 Hz) or the implementation of multiplexed interfaces to reduce connectivity.

Document WO2020025786A1 describes an apparatus and method using no switching elements for multiplexing and reading arrays of sensors whose electrical resistance is modulated by the signals to be measured. Sensor elements are arranged in group and columns where each column is fed with a continuous voltage waveform of different amplitude, frequency and phase characteristics which then produce current signals that are modulated by the variable resistance signals to be measured. Modulated currents are summed row-wise and collected at the read-out circuits, either by applying a constant voltage to each row of the array or by connecting a capacitor and converting these current summations into output voltage signals. The read-out circuits de-multiplex each individual sensor signal to be measured by means of lock-in demodulation according to the frequencies and phases employed for the stimulation of each column.

Document WO2020094898A1 describes flexible matrices of graphene field effects transistors with epicortical and intracortical configurations, which can register infra-slow signals and signals in a bandwidth that is typical of local field potentials. The invention is based on the graphene transistor system for measuring electrophysiological signals, comprising a processing unit and at least one graphene transistor with the graphene as the channel material contacted via two terminals, to which a variable voltage source is joined at the drain and source terminals of the transistor, with a reference as a gate terminal, and at least one filter for acquiring and dividing the signal of the transistor into at least two frequency bands, low and high, in which the first and second signals are amplified respectively with a gain value.

Currently, these devices require a DC coupling operation to fix the optimal bias point. This fact limits the compliance with IEC60601-1 regulation applicable to medical equipment, which limits maximum low frequency (DC) leakage current through a patient. This leakage current must be less than 10 μA in normal operation and less than 50 μA in case of simple failure. During a normal operation, the leakage current is controlled by the gSGFET gate impedance, being in the range of 1 nA (3 orders of magnitude below the minimum stablished by the regulation). However, in the case of simple failure (i.e. bias voltage exceeds the potential windows of gSGFET due to an electronics breakdown), the leakage current is not limited by any passive electronic component.

DESCRIPTION OF THE INVENTION

The present invention defines a device that limits the leakage current and at the same time allows the bias point control on electrophysiological signal recording systems, preferably neural signals. This device could be used with any kind of active transducer, but preferably with solution gated graphene field effect transistors (gSGFETs).

The device comprises an active transducer intended to contact a body tissue, for example a brain tissue, as well as three passive components. These components will limit the leakage current in any case, even in the case of electronics breakdown (IEC60601-1 simple failure scenario).

Specifically, the device comprises an active transducer, connected to a transimpedance amplifier, where its gain is fixed by first resistor (RG). The active transducer is also connected, opposite to the transimpedance amplifier, to a direct voltage source and an alternate voltage source, positioned in parallel.

The three passive components which the device also comprises and that limit the leakage current are a first capacitor (Cs) connected between the alternate voltage source and the active transducer, a second resistor (RDC) connected between de direct voltage source and the active transducer, in parallel with the first capacitor (Cs) and the alternate voltage source, and a second capacitor, connected between the active transducer and the transimpedance amplifier.

Particularly, the second resistor (RDC) limits the maximum leakage current and allows to set the voltage bias point, and the first and second capacitor block any DC current while allowing the pass of AC current which contains the recorded signal.

DESCRIPTION OF THE DRAWINGS

To complement the description being made and in order to aid towards a better understanding of the characteristics of the invention, in accordance with a preferred example of practical embodiment thereof, a set of drawings is attached as an integral part of said description wherein, with illustrative and non-limiting character, the following has been represented.

PREFERRED EMBODIMENT OF THE INVENTION

With the help of FIGS. 1 to 11, a preferred embodiment of the present invention is described below.

Figure 1:
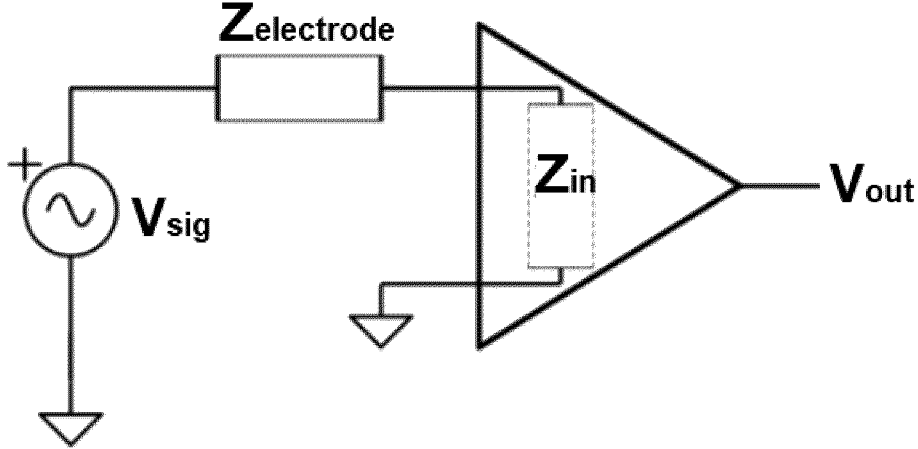
FIG. 1—Shows a schematic of an acquisition system based on electrodes from the state of the art.
Figure 2:
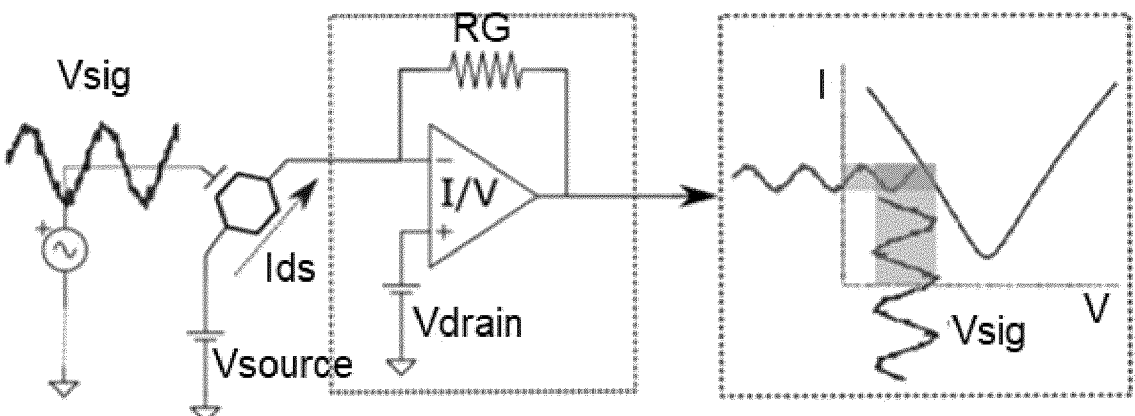
FIG. 2—Shows a schematic of an acquisition system based on active transducer (gSGFET) from the state of the art.
Figure 3:
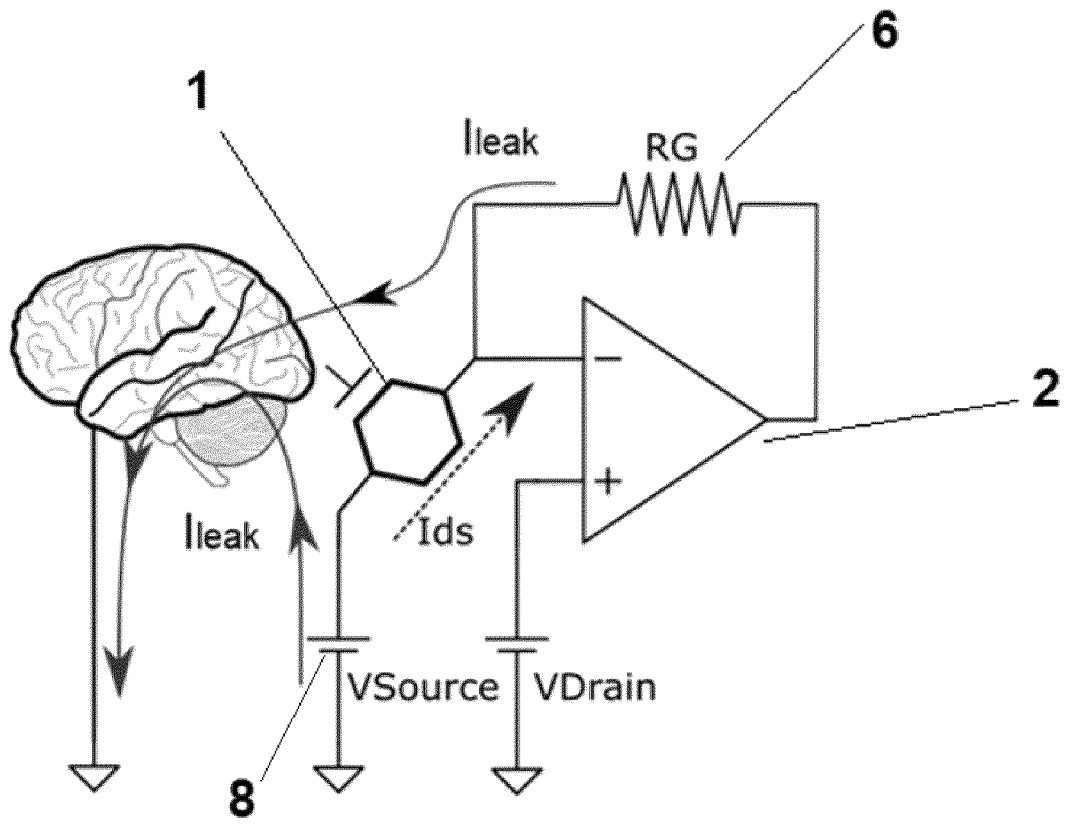
FIG. 3—Shows a schematic of a DC coupling device from the state of the art.

FIG. 3 shows a DC coupling system, which comprises an active transducer (1), connected to a signal acquisition module, comprised of a transimpedance amplifier (2) with a gain fixed by a first resistor (RG) (6). The active transducer (1) is connected to a first direct voltage source (8), as well as the transimpedance amplifier (2). Represented with a dotted-line arrow is the active transducer (1) current and with a continuous-line arrow is the patient leakage current. The object of the present invention is to eliminate said patient leakage current.

Figure 4:
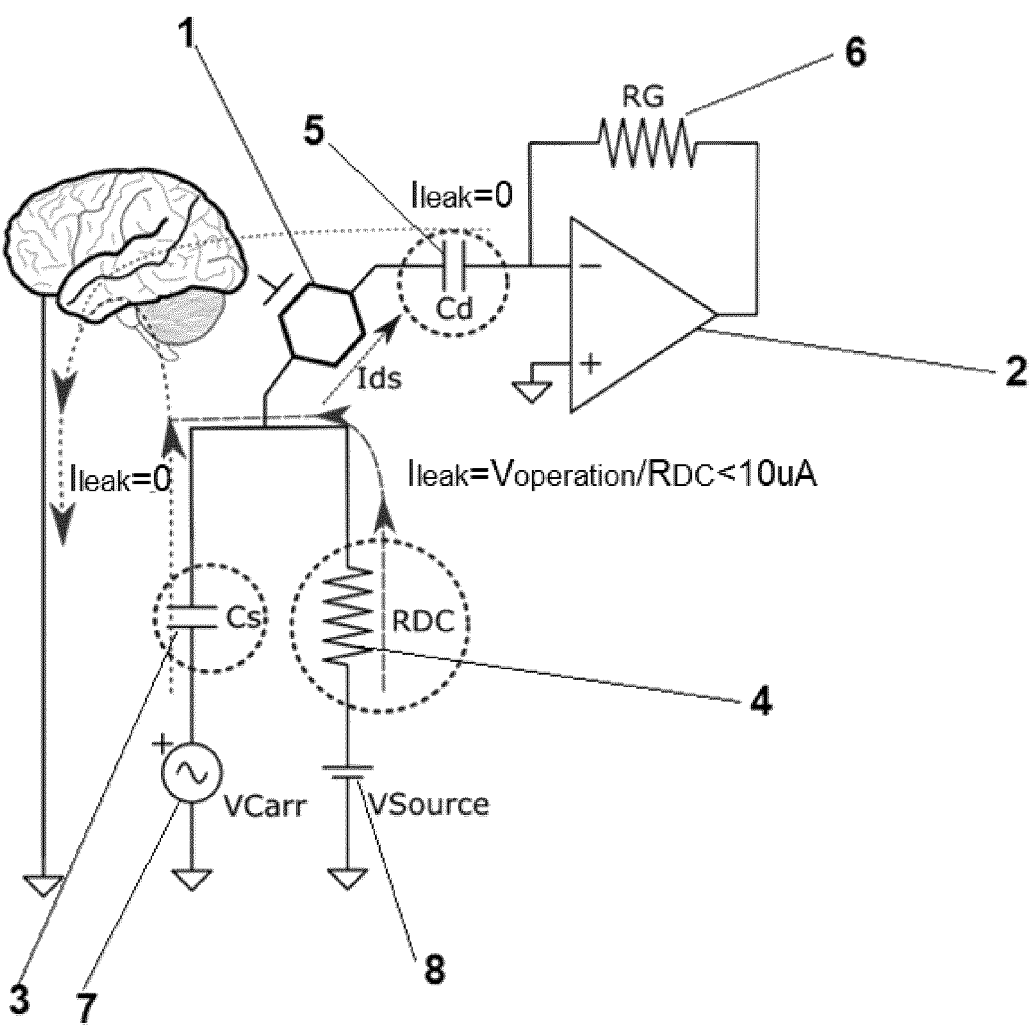
FIG. 4—Shows a schematic of an AC coupling device, which is the acquisition device.

FIG. 4 represents the device object of the present invention, an AC coupling system, which also comprises an active transducer (1), connected to a transimpedance amplifier (2) with a gain fixed by a first resistor (RG) (6). The active transducer (1) is connected to an alternate voltage source (7) and to a direct voltage source (8).

As shown in FIG. 4, the device comprises additionally a first capacitor (Cs) (3) connected between the alternate voltage source (7) and the active transducer (1), a second resistor (RDC) (4) connected between the direct voltage source (8) and the active transducer (1), in parallel with the first capacitor (Cs) (3) and the alternate voltage source (7), and a second capacitor (Cd) (5), connected between the active transducer (1) and the transimpedance amplifier (2).

In FIG. 4, Ids represents the active transducer (1) current, lined arrows indicate the patient leakage, which is limited by the second resistor (4) and dotted arrows indicate the patient leakage current, which blocked by both capacitors (3,5). All three circled elements are passive components that limit the leakage current. Particularly, the second resistor (RDC) (4) limits the maximum leakage current and allows to set the voltage bias point, and the first and second capacitors (3, 5) block any DC current while allowing the pass of AC current which contains a recorded signal.

The second resistor (4) and the capacitors (3, 5) limit the leakage currents, but at same time, limit the DC current through the active transducer (1) (Ids). Therefore, an AC signal coupling strategy must to be used for the neural signal acquisition instead of the DC signal coupling.

In an AC signal coupled system, the active transducer (1) behaves as a signal mixer between a carrier signal and an electrophysiological signal, allowing the use of amplitude modulation (AM) techniques for the signal amplification and processing.

The AM modulation consists on a mixer that multiplies a carrier signal and a modulator signal. The carrier wave (Wc) is a high frequency signal, where its amplitude will be a function of the modulator signal (Wm). The modulator signal can be recovered by a demodulation process, which consists on a product detector, as the one shown in FIG. 5. The input signal is multiplied by a carrier signal produced with a local oscillator to move the signal to the baseband, then a low pass filter (9) removes remaining high frequency components.

Figure 5:
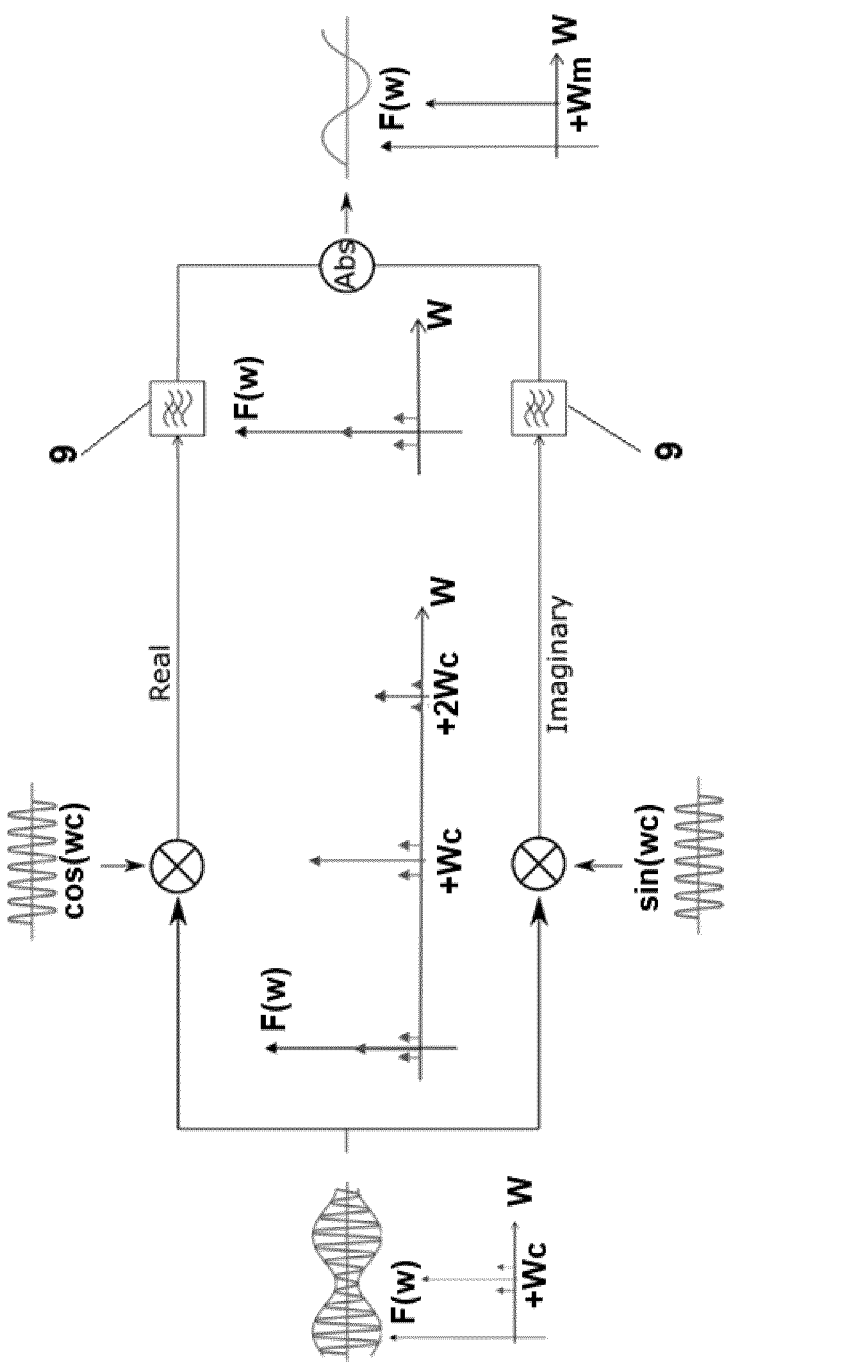
FIG. 5—Shows a block diagram of a product detector.

In FIG. 5, the block diagram of a product detector is presented. AM signal is multiplied by a local carrier signal of frequency $w_c$ with 0° phase (cosinus) to obtain real part and 90° phase (sinus) to obtain imaginary part. The low pass filter (9) is used to remove the high frequency components. The original signal (Wm) is recovered by computing the absolute value.

Figure 6:
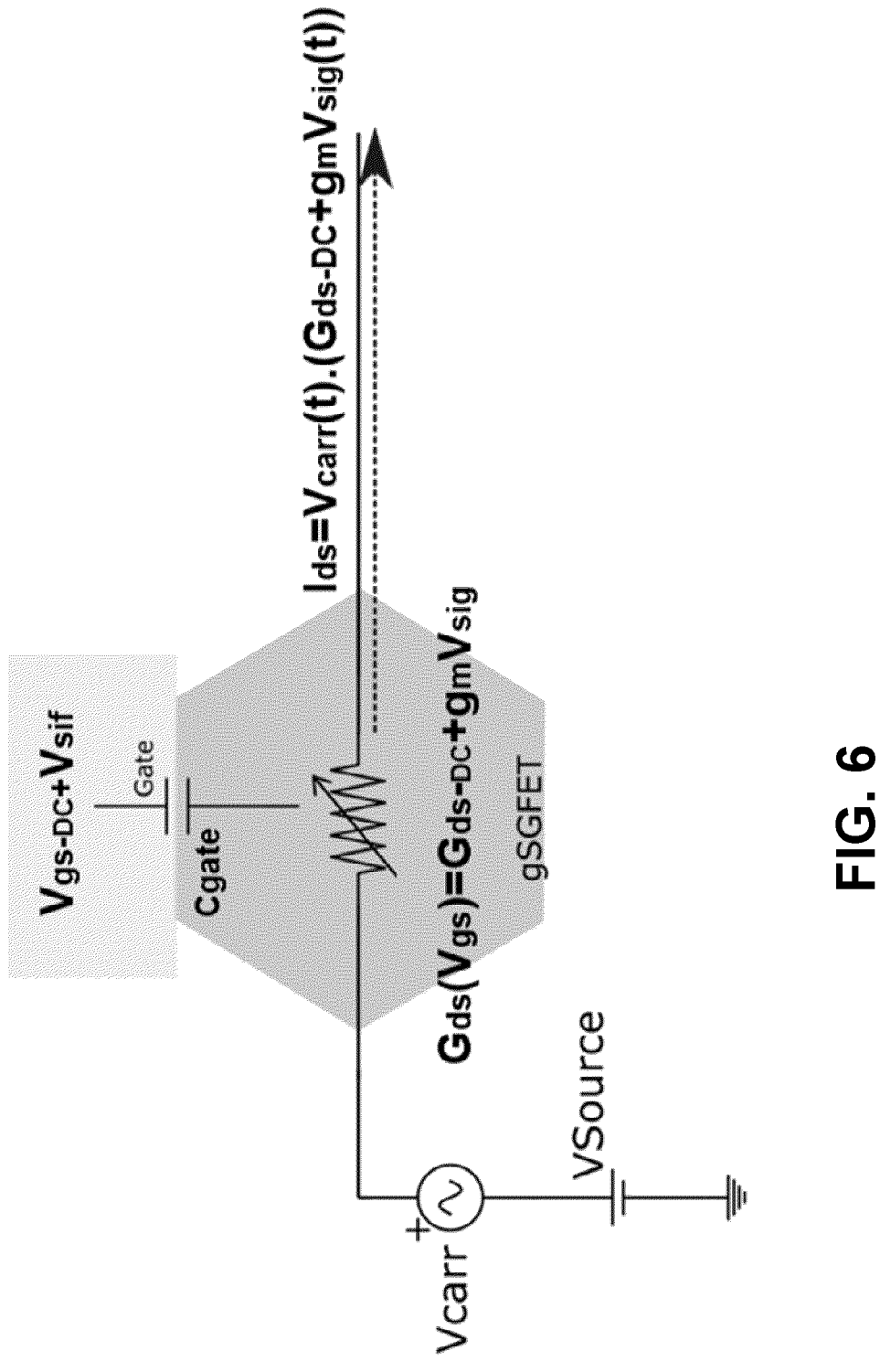
FIG. 6—Shows a schematic representation of a graphene transistor (gSGFET) working as a mixer.

In a preferred embodiment of the present invention a graphene transistor can be used as the active transducer (1). The graphene transistor (1) can be used as a mixer to implement an AC coupled acquisition system. In this case, an electrical potential fluctuation applied on its gate (i.e neural signal) changes the conductivity of the channel through the gate capacitance. Therefore, applying a pure tone voltage signal on the graphene transistor (1) source (Vcarr), the current through the channel (Ids) results from the product of Vcarr(t)·Vsig(t), as shown in FIG. 6, where Vsig(t) is the brain signal applied in the gate of the graphene transistor (1) (Vgs).

Figure 7:
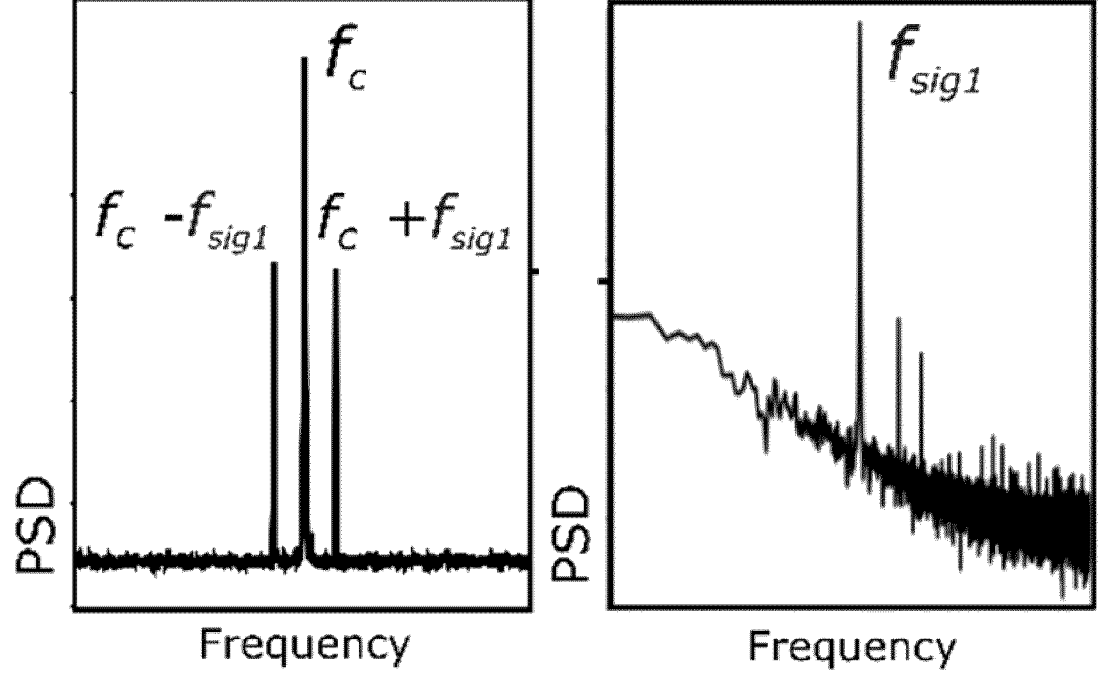
FIG. 7—Shows the power spectral density (PSD) of a modulated and demodulated signal.

The multiplication of those signals produces the folding of their frequencies, as can be seen in FIG. 7—left, where a peak at the carrier frequency (fc) is observed, with an amplitude proportional to channel resistant Rds–DC, with two side bands at $fc-fsig_1$ and $fc+fsig_1$ which are proportional to Vsig/gm. The gate signal $fsig_1$ is obtained after the demodulation process, as shown in FIG. 7—right.

For an optimal device operation, it is needed to control the bias point. The gate source DC voltage coming from the DC voltage source (8) must be fixed at a certain value according with the environmental conditions and the graphene transistor (1) performance. For that, the second resistor (Rdc) (4) is placed in parallel to the first capacitor (Cs) (3), which is connected to the DC voltage source (8).

Figure 8:
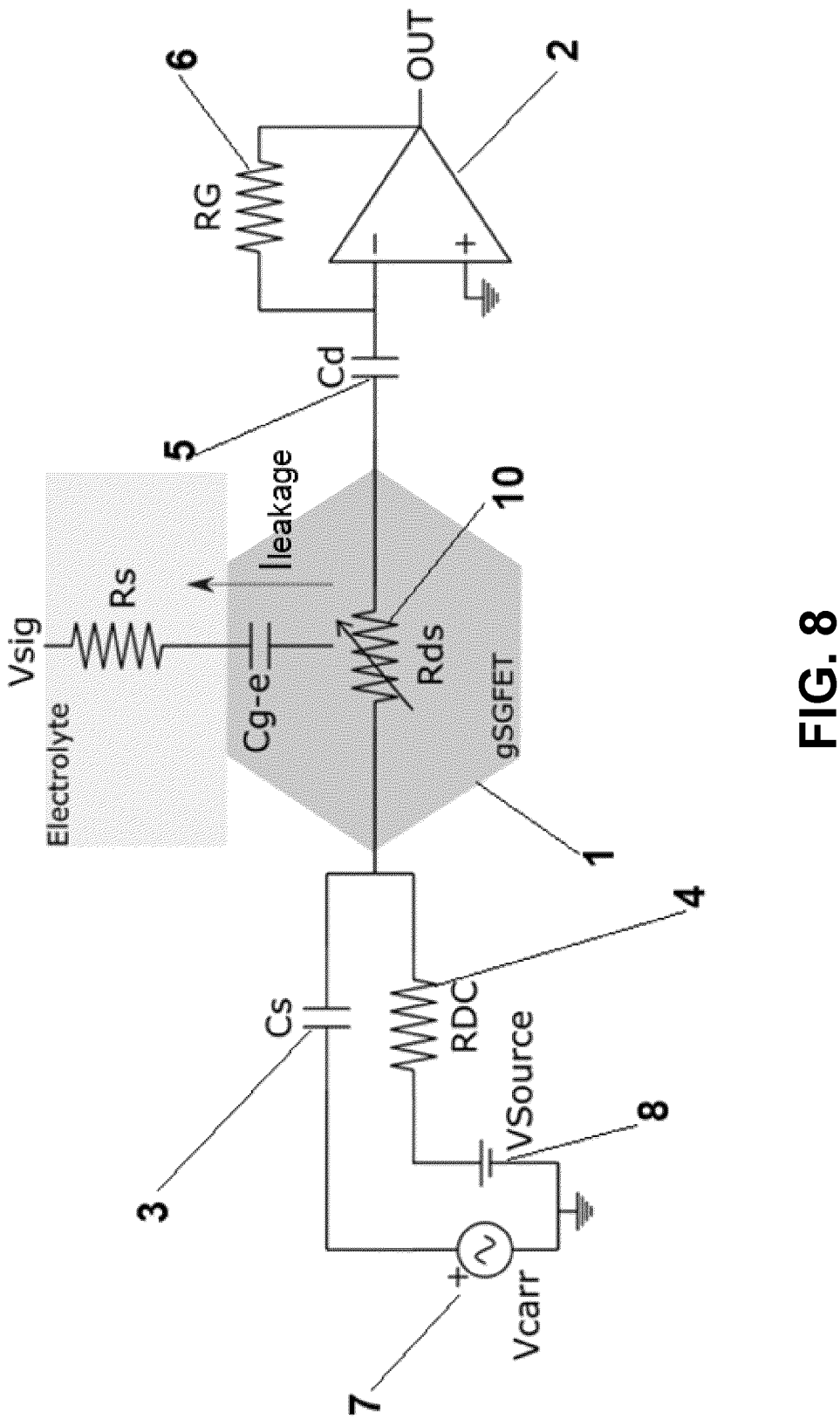
FIG. 8—Shows a graphene transistor (gSGFET) equivalent circuit connected to AC coupled system.

FIG. 8 shows the graphene transistor (1) equivalent circuit connected to the transimpedance amplifier (2) together with the protective elements second resistor (4) and capacitors (3, 5). It can be observed how the DC current circulating through the graphene transistor (1) is approximately zero in a stationary regime, when the gate capacitance (Cg-e) of the graphene transistor (1) and protective capacitances (3, 5) are charged at the bias voltage (Vsource) coming from the DC voltage source (8).

If any electronics or device failure occurs, the maximum allowed leakage current will be limited by the second resistor (4). To accomplish with the regulation, the second resistor's (4) value should be high enough to limit the current through itself to a maximum value of 50 µA. For that, the worst-case scenario is chosen, which is the case where any of the circuit nodes have the maximum voltage (the electronics supply voltage Vsupp). Thus, the value of the second resistor (4) have to be chosen higher than Vsupp/50 uA.

Figure 9:
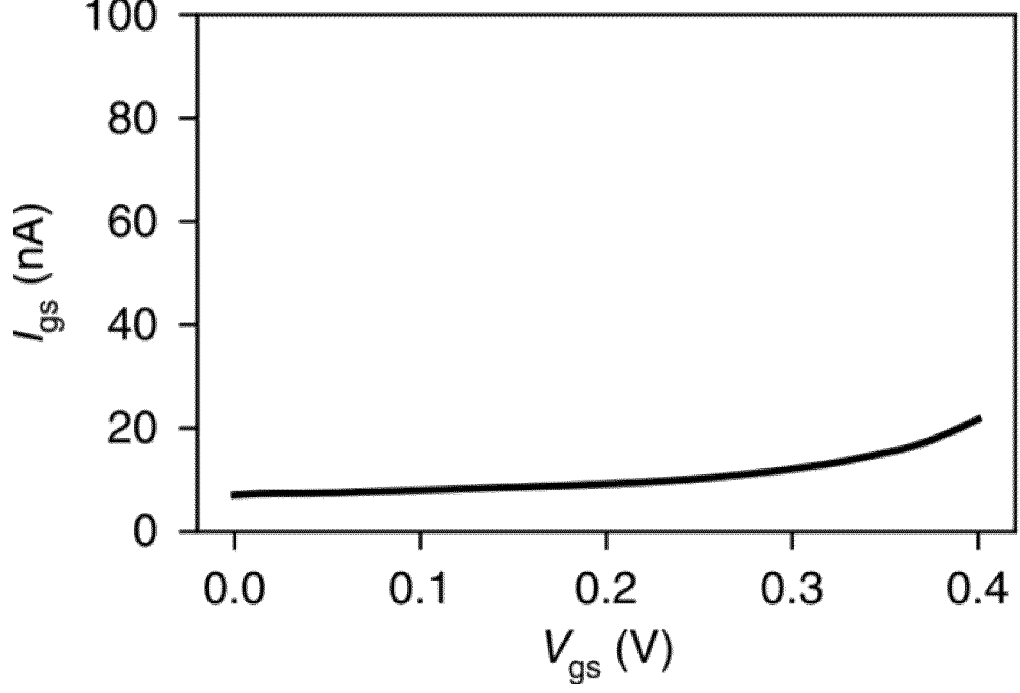
FIG. 9—Shows the leakage current through Cg-e during normal operation mode.

FIG. 9 shows the leakage current through the gate capacitance (Cg-e) of the graphene transistor (1), during normal operation mode, which is lower than 10 µA, meeting the IEC60601-1.

To achieve a correct functionality of the device, the value of the second capacitor (Cd) (5) and first capacitor (Cs) (3) should be chosen according with the frequency of the carrier signal (Fc) that the AC voltage source (7) introduces to avoid signal attenuation.

For the first capacitor Cs (3) capacitance value, it has to be considered that it is in series with a channel resistance (Rds) (10) of the graphene transistor (1), as shown in FIG. 8. Accordingly, the first capacitor (3) value has to accomplish the following expression:

$$f_c > \frac{1}{2 \cdot \pi \cdot C_s \cdot (R_{ds} \, / \! / \, R_{DC})}$$

For Cd capacitance value, it has to be considered the channel resistance Rds (10).

$$f_c > \frac{1}{2 \cdot \pi \cdot C_d \cdot R_{ds}}$$

Typically, electrophysiological applications require several recording sites, and at the same time minimizing the number of connection wires. For this reason, the graphene transistors (1) can be arranged in arrays where the source terminal is shared by all the graphene transistors (1) inside the array.

Figure 10:
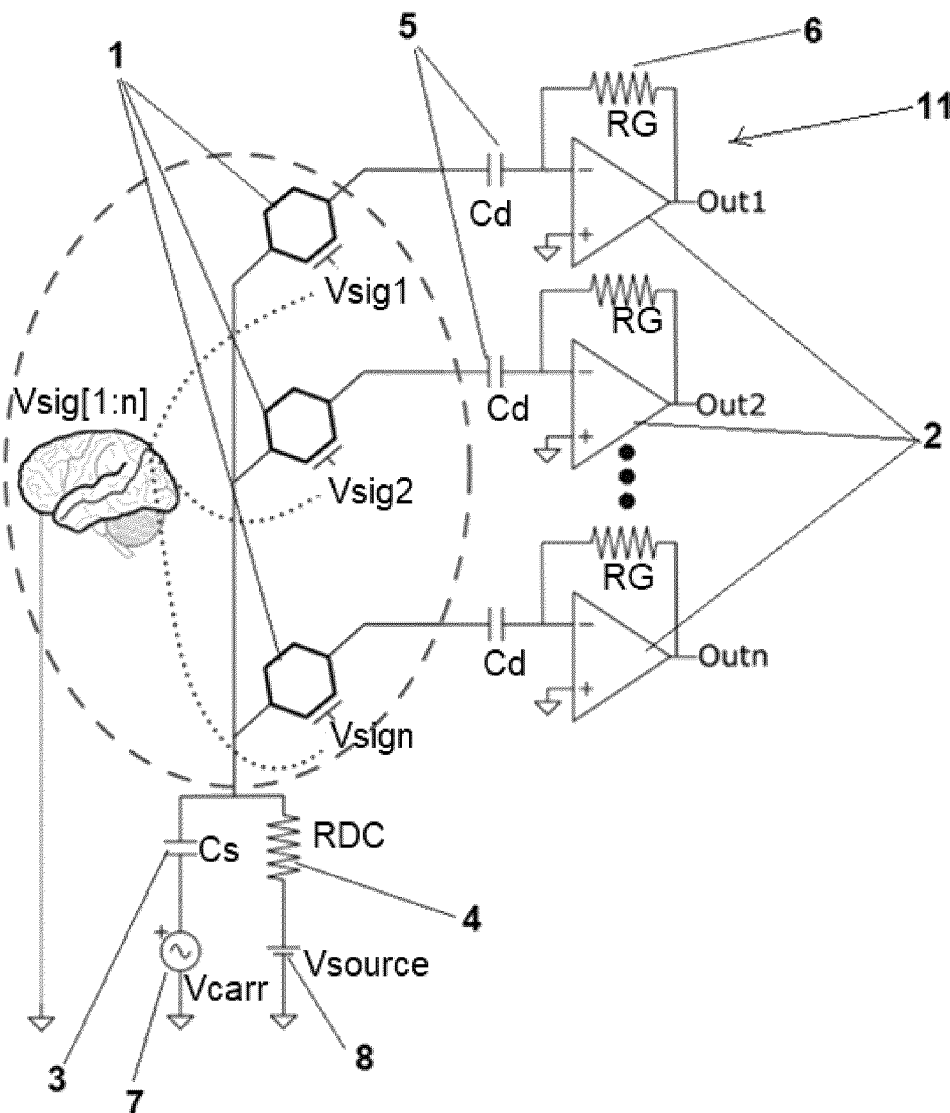
FIG. 10—Shows the multiple active transducer acquisition device "n" rows.

FIG. 10 shows how to implement the leakage current limitation in this kind of arrays. In this case, a unique first capacitor (3), second resistor (4) group is necessary because all the graphene transistors (1) use the same carrier signal, introduced by the AC voltage source (7), and are biased at the same working point. On the other hand, each graphene transistor (1) acquires a different electrophysiological signal, then different second capacitors (Cd) (5) need to be placed between each graphene transistor (1) and each transimpedance amplifier (2).

Figure 11:
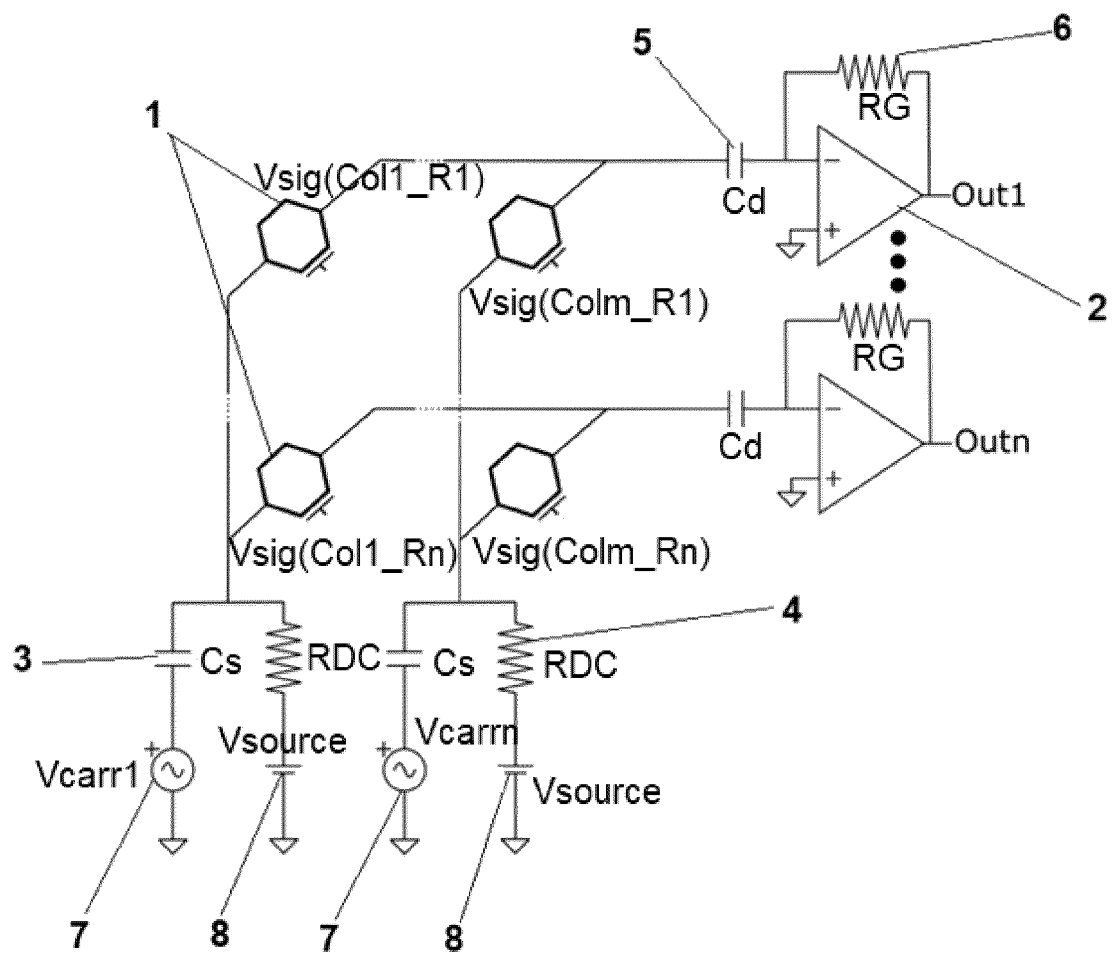
FIG. 11—Shows the multiplexed array acquisition device with "m" columns and "n" rows.

As commented, graphene transistors (1) can be used in multiplexed arrays to minimize the wiring connectivity. In FIG. 11, the arrays are arranged in "m" columns and "n" rows, implementing m×n recording sites while the wires needed for the connections is just n+m.

To implement the proposed protection in this kind of arrays, as shown in FIG. 11, the first capacitor (Cs) (3), second resistor (RDC) (4) group should be placed at each column, to provide the carrier signal and bias voltage to each one of the graphene transistors (1), and the second capacitor

6

(Cd) (5) should be placed between each row and the transimpedance amplifier (2), as in the case of the non-multiplexed arrays.

The work leading to this patent application has received funding from the European Union's Horizon 2020 Research and Innovation Programme under Grant Agreements No. 649953 (Graphene Flagship) and No. 732032 (BrainCom). We also acknowledge funding the 2DTecBio project (FIS2017-85787-R) funded by the Spanish Ministry of Science, Innovation and Universities, the Spanish Research Agency (AEI) and the European Regional Development Fund (FEDER/UE); and the European Regional Development Funds (ERDF) allocated to the Programa operatiu FEDER de Catalunya 2014-2020, with the support of the Secretaria d'Universitats i Recerca of the Departament d'Empresa i Coneixement of the Generalitat de Catalunya for emerging technology clusters devoted to the valorization and transfer of research results (GraphCAT 001-P-001702).

The invention claimed is:

1. An acquisition device to limit leakage current in electrophysiological signal recording devices, the acquisition device comprising:
    a first active transducer connected to a first transimpedance amplifier and intended to contact a body tissue;
    an alternate voltage source connected to the first active transducer and is opposite to the first transimpedance amplifier;
    a direct voltage source connected to the first active transducer, parallel to the alternate voltage source;
    a first capacitor connected between the alternate voltage source and the first active transducer;
    a first resistor connected between the direct voltage source and the first active transducer, parallel to the first capacitor and the alternate voltage source; and
    a second capacitor connected between the first active transducer and the first transimpedance amplifier.

2. The device according to claim 1, wherein the first active transducer is a graphene transistor (gSGFET).

3. The device according to claim 1, wherein the resistance of the first resistor is higher than Vsupp/50 uA, being Vsupp a maximum supply voltage of the direct voltage source.

4. A multiple active transducer acquisition device comprising:
    an acquisition device, the acquisition device comprising:
        a first active transducer connected to a first transimpedance amplifier and intended to contact a body tissue;
        an alternate voltage source connected to the first active transducer and is opposite to the first transimpedance amplifier;
        a direct voltage source connected to the first active transducer, parallel to the alternate voltage source;
        a first capacitor connected between the alternate voltage source and the first active transducer;
        a first resistor connected between the direct voltage source and the first active transducer, parallel to the first capacitor and the alternate voltage source; and
        a second capacitor connected between the first active transducer and first the transimpedance amplifier; and
    one or more acquisition modules, each of the one or more acquisition modules comprising:
        a second active transducer;
        a third capacitor connected to the second active transducer;
        a second transimpedance amplifier connected to the third capacitor; and a second resistor connected in parallel with the second transimpedance amplifier; and wherein the second active transducer of each acquisition module is connected parallel with the first active transducer of the acquisition device opposite to the third capacitor.

5. The device according to claim 4, wherein the first active transducer and the second active transducer are graphene transistors (gSGFET).

6. A multiplexed array acquisition device comprising:

"m×n" active transducers situated in each "m×n" position of a matrix with "m" columns and "n" rows;

m common first capacitors;

m common first resistors;

m common alternate voltage sources; and m common direct voltage sources;

wherein each common first resistor is connected in parallel to each common first capacitor, and each common first capacitor is connected to each common alternate voltage source and each common first resistor is connected to each common direct voltage source;

n common second capacitors;

n common transimpedance amplifiers; and n common second resistors;

wherein each common second capacitor is connected to each common transimpedance amplifier and each common second resistor is connected parallel to each common transimpedance amplifier; and wherein:

the active transducers situated in each column of the matrix are connected to each common first capacitor and each common first resistor, and the active transducers situated in each row of the matrix are connected to each common second capacitor.

7. The device according to claim 6, wherein the active transducers are graphene transistors (gSGFET).

\* \* \* \* \*